United States Patent
Cerati et al.

(10) Patent No.: US 7,326,939 B2
(45) Date of Patent: Feb. 5, 2008

(54) METHOD AND DEVICE FOR QUALITY CONTROLLING PACKETS

(75) Inventors: Luca Cerati, Bologna (IT); Gaetano De Pietra, Casalecchio Di Reno (IT)

(73) Assignee: G.D Societa' per Azioni, Bologna (IT)

( * ) Notice: Subject to any disclaimer, the term of this patent is extended or adjusted under 35 U.S.C. 154(b) by 133 days.

(21) Appl. No.: 11/108,214

(22) Filed: Apr. 18, 2005

(65) Prior Publication Data
US 2005/0238352 A1 Oct. 27, 2005

(30) Foreign Application Priority Data
Apr. 19, 2004 (IT) .......................... BO2004A0221

(51) Int. Cl.
*G01T 1/00* (2006.01)
*H04B 10/08* (2006.01)
(52) U.S. Cl. ...................... 250/486.1; 398/33
(58) Field of Classification Search ............. 250/486.1, 250/559.2; 382/141; 53/131.4
See application file for complete search history.

(56) References Cited

U.S. PATENT DOCUMENTS

| | | | | |
|---|---|---|---|---|
| 4,166,973 A * | 9/1979 | Lilly et al. | ................... | 324/642 |
| 5,877,506 A | 3/1999 | Focke et al. | | |
| 5,928,948 A * | 7/1999 | Malchesky | ...................... | 436/2 |
| 5,943,388 A * | 8/1999 | Turner | ........................ | 378/98.9 |
| 5,978,499 A * | 11/1999 | Tossel et al. | ................ | 382/141 |
| 6,166,366 A * | 12/2000 | Lewis et al. | ............... | 250/208.1 |
| 6,173,551 B1 * | 1/2001 | Bowman et al. | ............ | 53/131.4 |
| 6,198,537 B1 * | 3/2001 | Bokelman et al. | ........... | 356/429 |
| 6,234,943 B1 * | 5/2001 | Copin | .......................... | 493/11 |
| 6,301,380 B1 * | 10/2001 | Mullins et al. | ............... | 382/141 |
| 6,384,359 B1 * | 5/2002 | Belcastro et al. | ............ | 209/536 |
| 6,385,333 B1 * | 5/2002 | Puckett et al. | ............... | 382/143 |
| 6,578,583 B2 * | 6/2003 | Smith et al. | ................ | 131/84.1 |
| 6,919,965 B2 * | 7/2005 | Koele et al. | ................. | 356/615 |
| 7,176,696 B2 * | 2/2007 | Cerati et al. | ................. | 324/633 |

FOREIGN PATENT DOCUMENTS

| | | |
|---|---|---|
| EP | 0 330 495 | 8/1989 |
| EP | 0 902 275 | 3/1999 |

* cited by examiner

*Primary Examiner*—David Porta
*Assistant Examiner*—Faye Boosalis
(74) *Attorney, Agent, or Firm*—Marshall, Gerstein & Borun LLP

(57) ABSTRACT

A method and device for quality controlling packets of cigarettes, whereby, as a packet is fed, in use, through a quality control station, an optical detecting unit acquires data relative to given portions of the packet, which portions are coated with material optically detectable at wavelengths outside the visible range; the data detected by the optical detecting unit is compared with reference data, and the outcome of the comparison is used to determine acceptance or rejection of the packet; in this way, the condition of the packet can be determined regardless of the graphics on the packet.

27 Claims, 10 Drawing Sheets

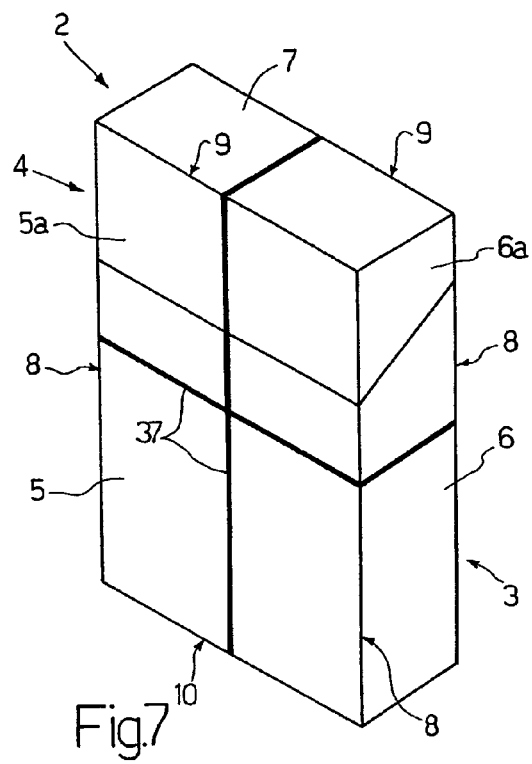
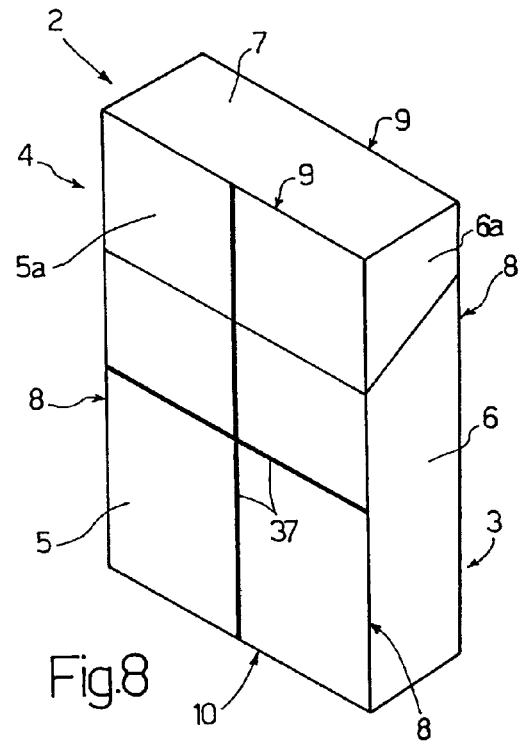
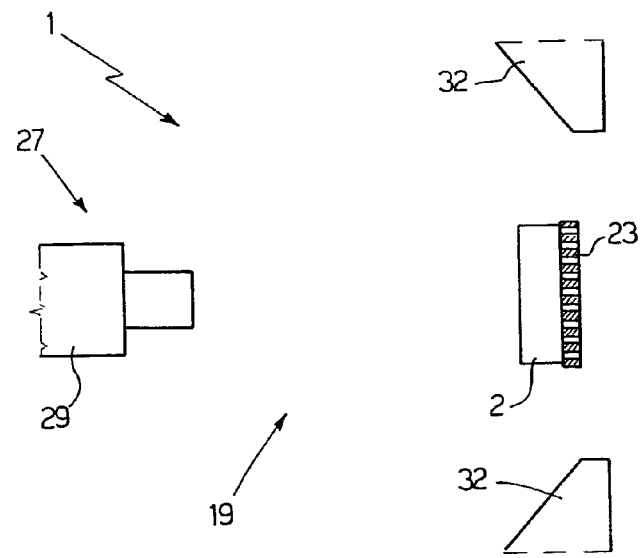

US 7,326,939 B2

METHOD AND DEVICE FOR QUALITY CONTROLLING PACKETS

CROSS-REFERENCE TO RELATED APPLICATION

This application claims the benefit of Italian patent application number BO2004A 000221, filed Apr. 19, 2004.

The present invention relates to a method and device for quality controlling a packet; to a packet; and to a relative blank.

The present invention may be used to advantage in packing cigarettes, to which the following description refers purely by way of example.

BACKGROUND OF THE INVENTION

Packets produced on a packing machine are normally quality controlled to determine any defects, in particular, stains, scratches, or dents; and any faulty packets are subsequently rejected.

In U.S. Pat. No. 4,912,554, a packet is fed along a path through a quality control station where television cameras acquire an image of the packet; and the image is compared with a reference image to determine whether or not the packet is to be rejected.

Though efficient, the known quality control system described above has been found to fall short in some respects in terms of versatility and sensitivity. In particular, whenever changes are made to the graphics (artwork, brands, and/or colours) on the outside of the packets (e.g. so-called "brand changes"), changes must also be made to the reference image. Moreover, in areas of the packet bearing complex and/or highly coloured images, defects such as scratches or dents are especially difficult to detect. In other words, the artwork and colours on the packet act as noise during detection.

U.S. Pat. No. 5,877,506 discloses a device, which is designed to monitor blanks and comprises a source of infrared radiation. Such a device is designed to monitor only the contours of the blanks in order to verify the supply of the correct blanks, when there is a change in the type of packaging to be manufactured, and the correct positioning of the blanks. The device disclosed in U.S. Pat. No. 5,877,506 is not designed to control the quality of the blanks and is not designed to monitor surfaces of the blanks.

SUMMARY OF THE INVENTION

It is an object of the present invention to provide a method and device for quality controlling a packet, designed to eliminate, at least partially, the aforementioned drawbacks, and which at the same time are cheap and easy to implement.

According to the present invention, there is provided a method of quality controlling a packet; the method comprising a feed step to feed the packet along a feed path through a quality control station; an optical detecting step to detect at least one detected data item relative to at least one given portion of the packet; and a comparing step to compare the detected data item with at least one reference data item to determine rejection or acceptance of the packet; the method being characterized in that the given portion comprises at least a pigment, which is optically detectable at at least one given wavelength outside the visible range; the detected data item being detected by receiving electromagnetic radiation having said given wavelength from said pigment.

According to the present invention, there is also provided a device for quality controlling a packet; the device comprising at least one optical detector for optically detecting at least one data item relative to at least one given portion of the packet; and a comparing unit for comparing the detected data item with at least one reference data item to determine rejection or acceptance of the packet; the device being characterized in that the optical detector is designed to detect the detected data item by receiving electromagnetic radiation, which, in use, comes from at least a pigment of the given portion and has at least one given wavelength outside the visible range; the comparing unit being designed to elaborate said detected data item relating to said electromagnetic radiation coming from the pigment.

According to the present invention, there is also provided a packet having at least one given portion optically detectable at at least one given wavelength outside the visible range; the given portion comprising at least one first line, and at least one second line crosswise to the first line; the first and second line extending at least from a first edge to a second edge of the packet.

BRIEF DESCRIPTION OF THE DRAWINGS

A number of non-limiting embodiments of the present invention will be described by way of example with reference to the accompanying drawings, in which:

FIG. 2 shows a larger-scale section along line II-II of the FIG. 1 device;

FIGS. 5 to 9 show front views in perspective of alternative embodiments of packets in accordance with the present invention;

DETAILED DESCRIPTION OF THE INVENTION

Figure 1:
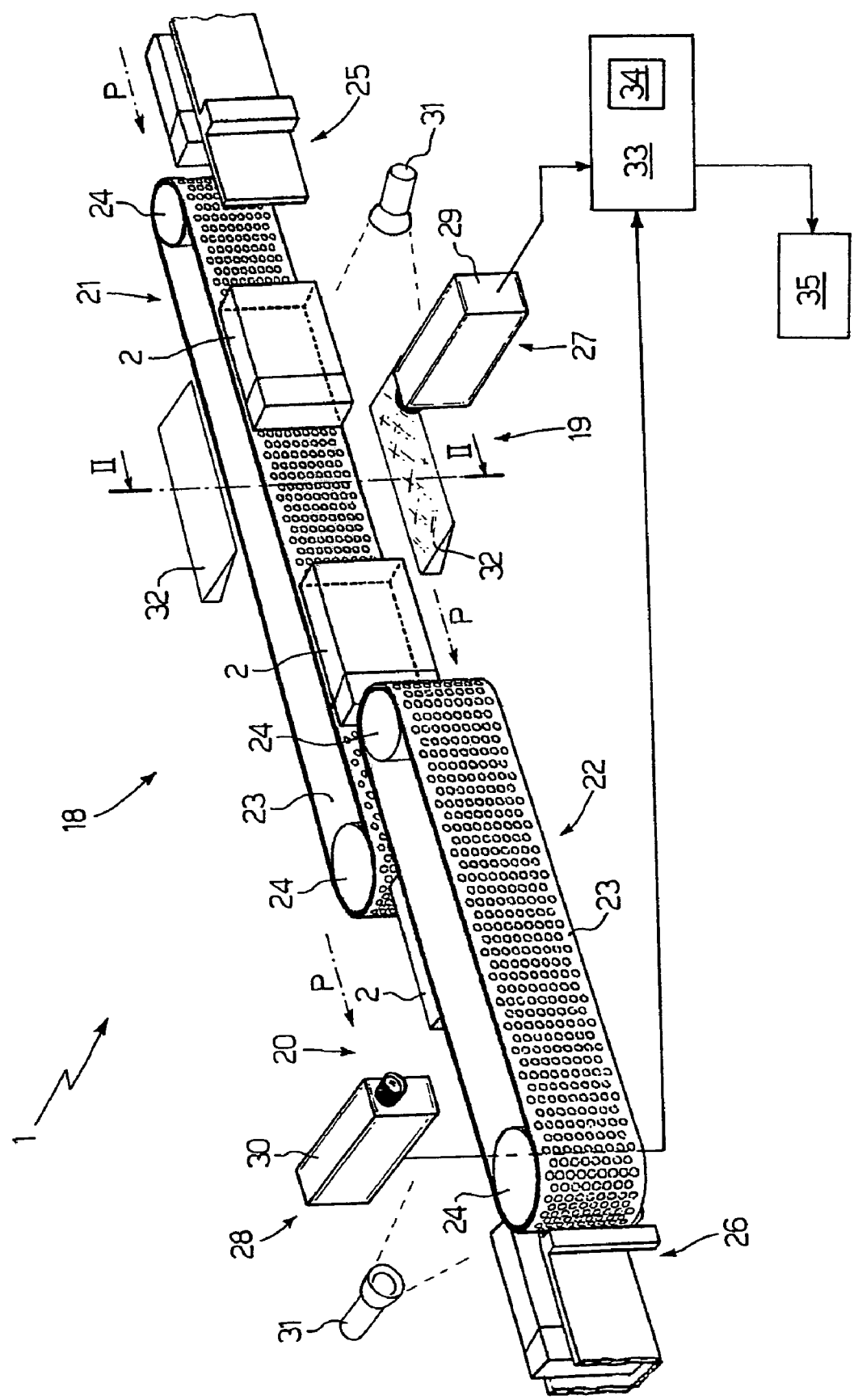
FIG. 1 shows a view in perspective, with parts removed for clarity, of a device for quality controlling packets in accordance with the present invention.
Figure 3:
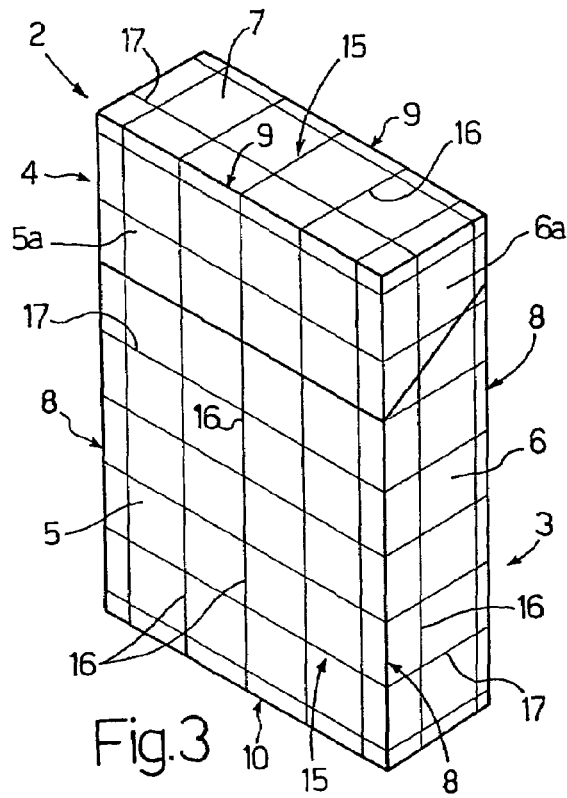
FIG. 3 shows a front view in perspective of a packet of cigarettes in accordance with the present invention.

Number 1 in FIG. 1 indicates as a whole a device for quality controlling a "rigid" packet 2 of cigarettes (FIG. 3). Packet 2 comprises a cup-shaped body 3, and a lid 4 hinged to cup-shaped body 3. Cup-shaped body 3 comprises a front wall 5, two lateral walls 6 (only one shown in FIG. 3), a bottom wall (now shown), and a rear wall (not shown). Lid 4 comprises a front wall 5a, two lateral walls 6a (only one shown in FIG. 3), a top wall 7, and a rear wall (not shown). Lateral walls 6 and 6a are connected to respective front walls 5 and 5a and to the respective rear walls (not shown) by relative longitudinal edges 8. Front wall 5a and the rear wall (not shown) of lid 4 are connected to top wall 7 by relative edges 9; and front wall 5 is connected to the bottom wall (not shown) by an edge 10.

Figure 4:
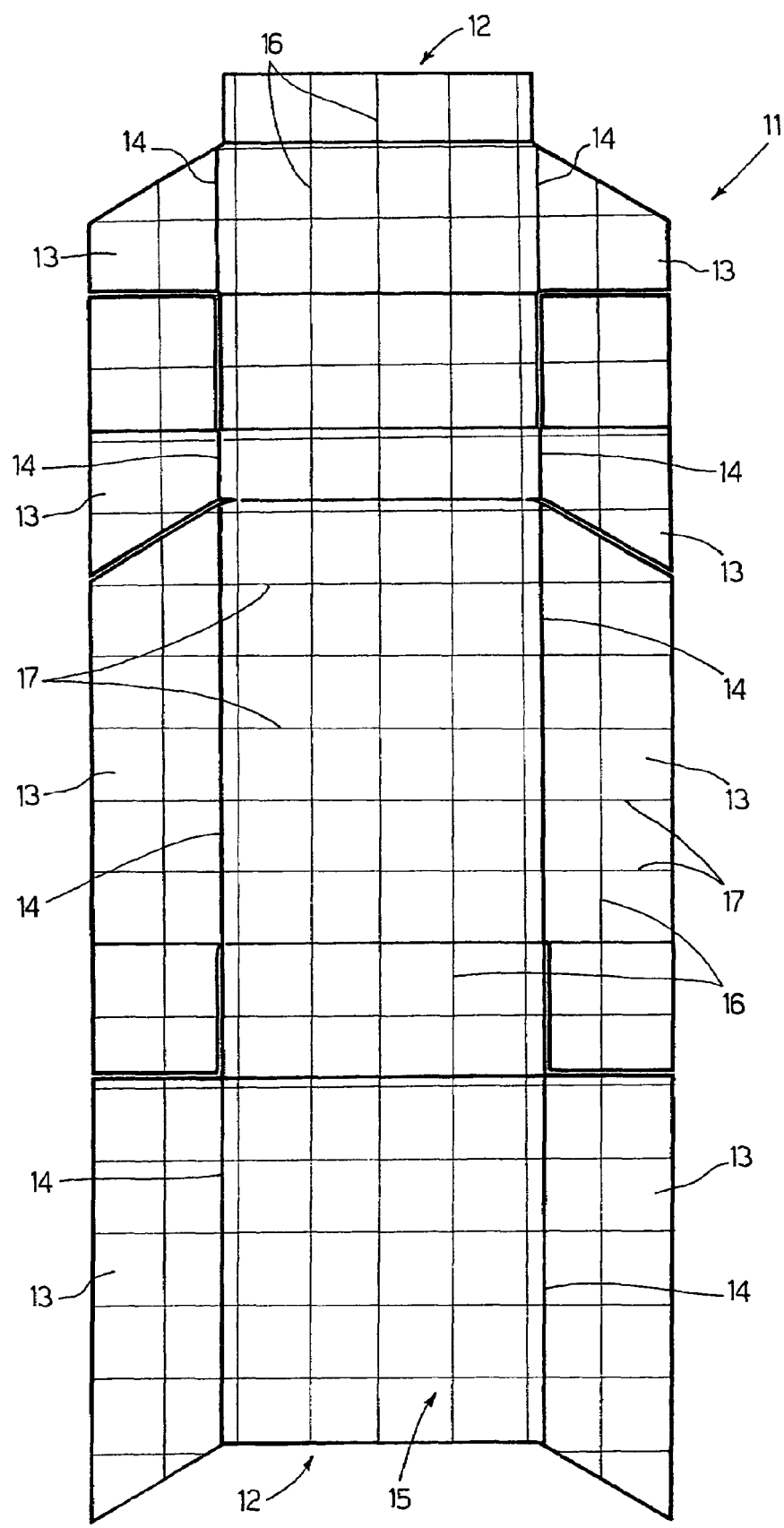
FIG. 4 shows a spread-out view of a blank by which to form the FIG. 3 packet.

Packet 2 is formed from a substantially flat blank 11 (FIG. 4) comprising a central portion 12, and a number of lateral panels 13 located symmetrically on opposite sides of portion 12. Portion 12 comprises a number of panels aligned lengthwise of blank 11; each panel 13 is connected to portion 12 by a preformed fold line 14; and, once folded, fold lines 14 correspond to edges 8 of packet 2.

Blank 11 has a grid 15 comprising a number of parallel longitudinal lines 16, and a number of parallel lines 17 crosswise, in particular, perpendicular, to lines 16. Lines 16 and 17 are invisible to the naked eye, and comprise special pigments detectable optically at a given wavelength outside the visible range, in particular at a wavelength in the ultraviolet range.

Device 1 (FIG. 1) comprises a transfer unit 18 for feeding packet 2 along a path P through two quality control stations 19 and 20. Device 1 also comprises two conveyors 21 and 22, each having a suction belt 23 positioned on edge and looped about two vertical-axis pulleys 24. Conveyor 21 receives packet 2 from an input station 25, and feeds packet 2 through quality control station 19 to conveyor 22; and conveyor 22 feeds packet 2 through quality control station 20 to an output station 26.

Two detecting units 27 and 28 are located at quality control stations 19 and 20 respectively, and each comprise an optical detector 29, 30, and an electromagnetic radiation source 31. Optical detectors 29 and 30 acquire data relative to grid 15 by receiving electromagnetic radiation at said given wavelength.

As shown more clearly in FIG. 2, two inclined mirrors 32 are located on opposite sides of conveyor 21 at quality control station 19, to enable optical detector 29 to analyze lateral walls 6 and 6a of packet 2.

Device 1 also comprises a central control unit 33 which receives the data acquired by detecting units 27 and 28, and in turn comprises a comparing unit 34 for comparing the acquired data with reference data. On the basis of the comparison between the acquired and reference data, central control unit 33 activates a known reject device 35 (shown schematically in FIG. 1) located immediately downstream from device 1 and for eliminating any faulty packets downstream from conveyor 22.

In actual use, when packet 2 is located at quality control stations 19 and 20, sources 31 emit electromagnetic radiation to bring the pigments to an excited state, decaying from which the pigments themselves emit electromagnetic radiation at said given wavelength outside the visible range. At this point, optical detectors 29 and 30 detect the shape and/or position of various areas of grid 15 and/or the intensity of the electromagnetic radiation, at the given wavelength, from the areas of grid 15.

The electromagnetic radiation emitted by sources 31 and the aforementioned pigments may have different wavelengths. In the case the electromagnetic radiation emitted by sources 31 and the aforementioned pigments have indeed different wavelengths, as optical detectors 29 and 30 detects electromagnetic radiation at the aforementioned given wavelength, noise due to, for example, radiation simply reflected by packet 2 is disregarded; as a consequence, the detection of data is more precise.

The detected shape, position, and/or intensity are compared by comparing unit 34 with a reference shape, position, and/or intensity; and, in the event the difference between the detected and reference data exceeds given threshold values, central control unit 33 activates reject device 35.

Figure 16:
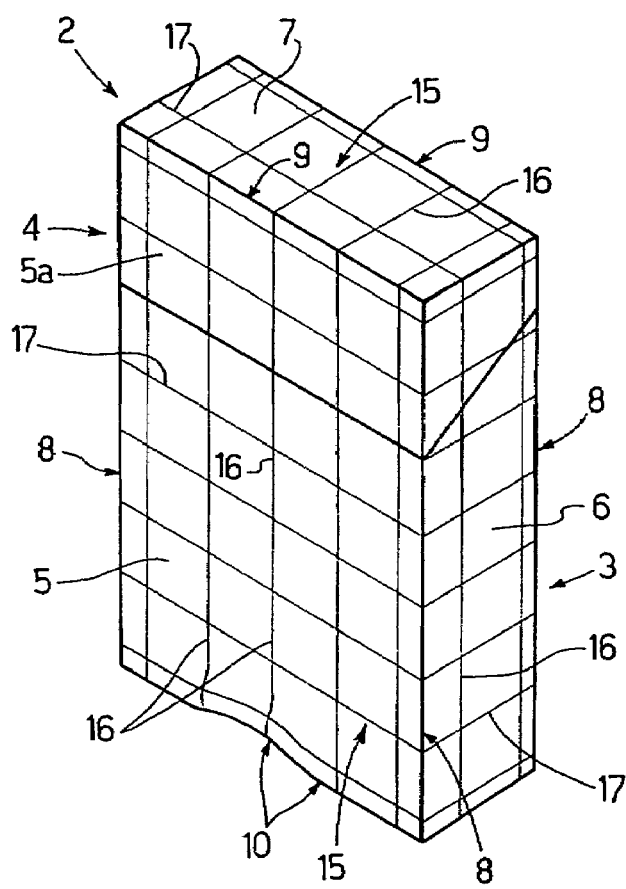
FIG. 16 shows a front view in perspective of a damaged FIG. 3 packet.

In connection with the above, it should be pointed out that, in the event packet 2 is dented, the shape and position of detected areas of grid 15 differ from the reference shape and position of packet 2 in perfect condition; and, in the event packet 2 is scratched, the intensity of the electromagnetic radiation, at the given wavelength, of the scratched area of grid 15 is below the reference intensity. FIG. 16 shows the FIG. 3 packet 2 with a dent along edge 10, and the relative distorted grid 15.

Figure 15:
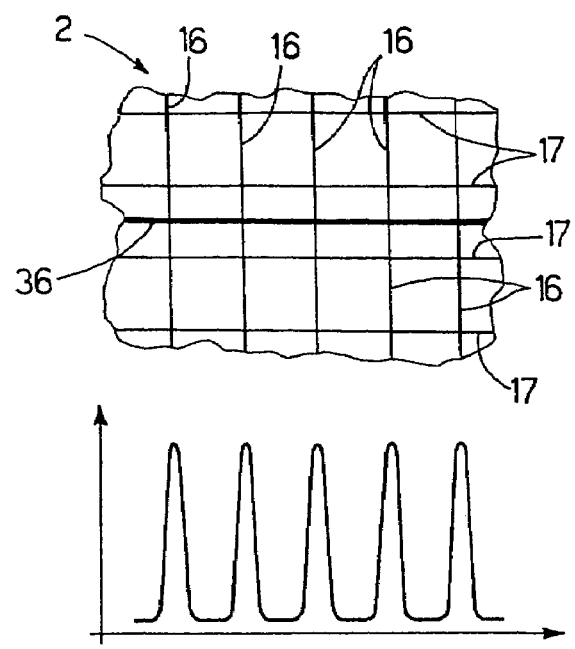
FIG. 15 shows a portion of the FIG. 3 packet and the corresponding response of a detecting device.

Optical detectors 29 and 30 preferably each comprise known area scales for detecting electromagnetic radiation, at the given wavelength, along scan lines 36. By way of example, FIG. 15 shows an area of grid 15, and the corresponding area scale response along scan line 36. The y axis shows the position along the scan line, and the x axis the intensity of the relative pixels. In this case, the comparing unit compares the positions, heights, and/or shapes of the peaks in FIG. 15 with reference positions, heights, and/or shapes.

Device 1 as described above allows changes to be made to the graphics (artwork, brands, and/or colours) on the outside of packet 2 (e.g. so-called "brand changes") without changing the reference data, and also provides for accurately determining the condition of packet 2, even in areas of packet 2 bearing complex and/or highly coloured images.

In this connection, it should be pointed out that, since optical detectors 29 and 30 only detect electromagnetic radiation at said given wavelength outside the visible range, whatever is picked up by optical detectors 29 and 30 is unaffected by the graphics on the outside of packet 2.

FIGS. 5 to 14 show alternative embodiments of packet 2 and relative blank 11. As can be seen, packets 2 in FIGS. 5 to 9 are substantially similar to packet 2 described above, except that grid 15 is replaced by one or more given portions 37 of various forms and comprising said pigments.

Grid 15 is preferably stamped on blank 11 off the packing machine, i.e. at the packing material manufacturer's plant or paper mill. Alternatively, the grid may be stamped on the blank by means of a stamping device upstream from the packing machine.

Figure 5:
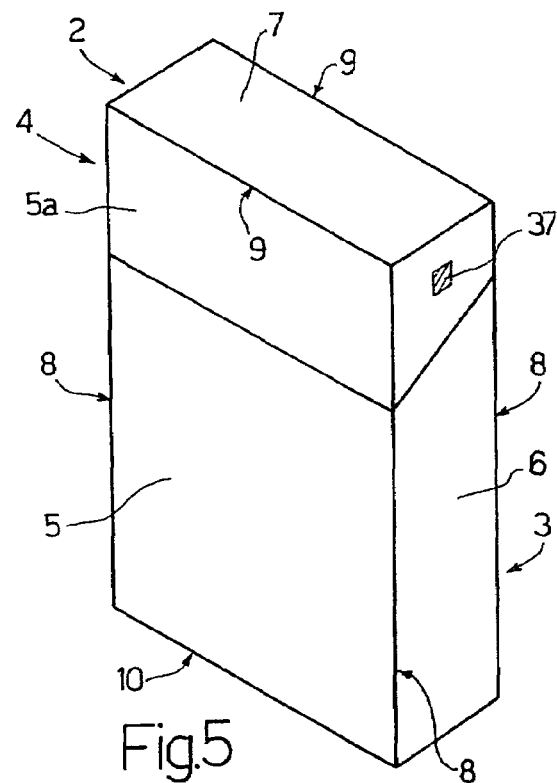
Figure 10:
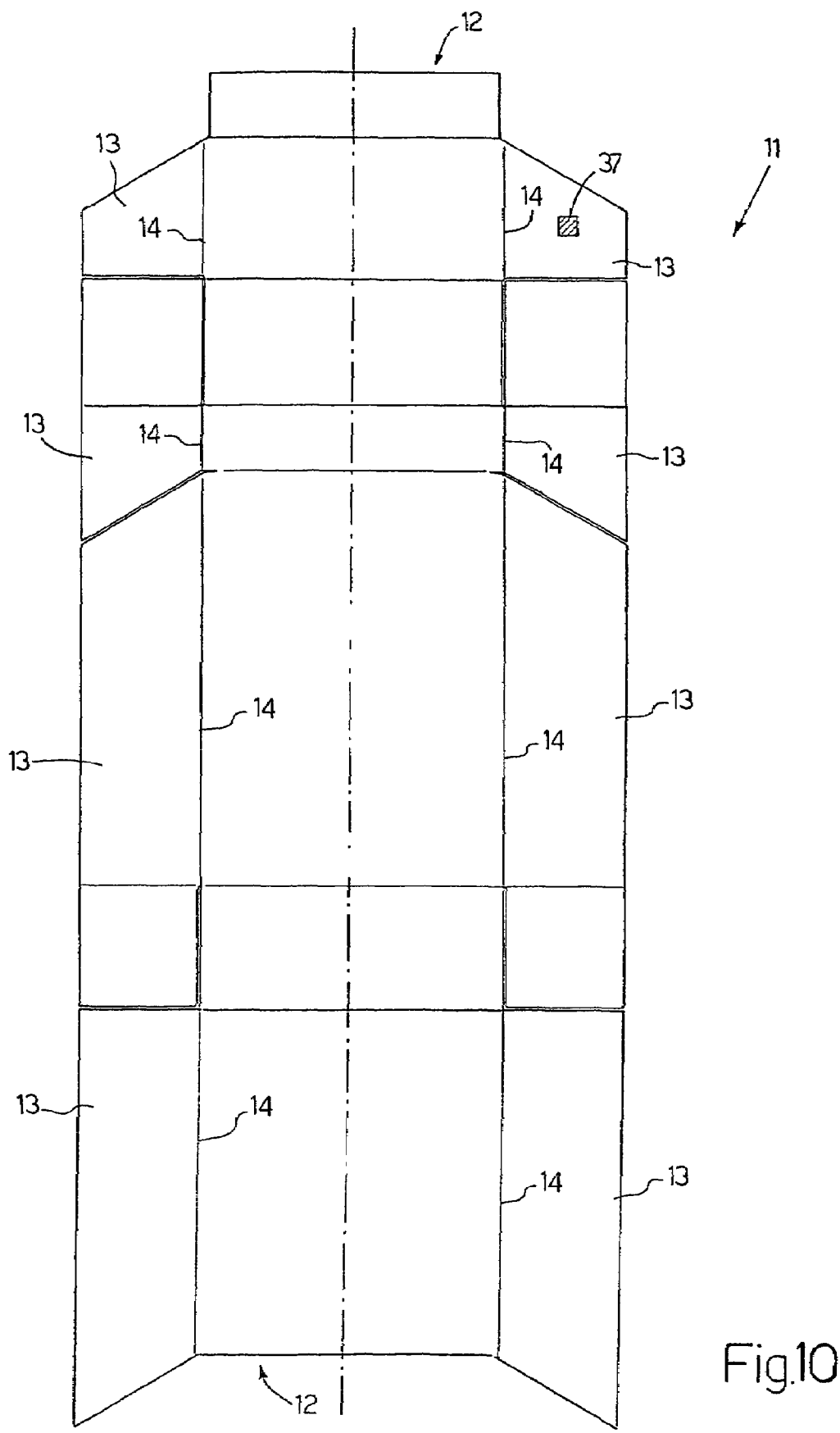
FIGS. 10 to 14 show spread-out views of blanks by which to form the FIG. 5 to 9 packets respectively.

The FIG. 5 packet 2, formed from the FIG. 10 blank, comprises one portion 37 on lateral wall 6a of lid 4. In this case, in the event the lateral panel 13 partly defining wall 6a is not glued properly and is therefore partly raised, optical detector 29 can detect portion 37 directly, and not only by means of one of mirrors 32. In FIGS. 5 and 10, portion 37 is hatched.

Figure 6:
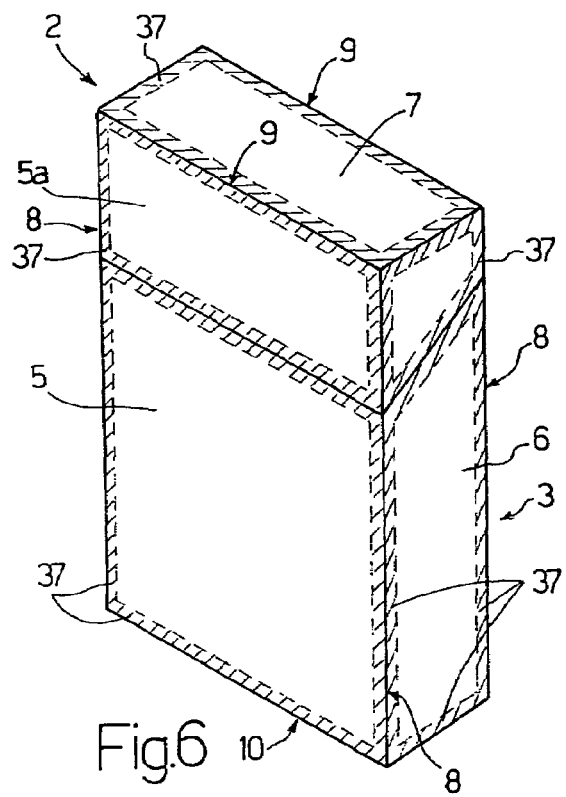
Figure 11:
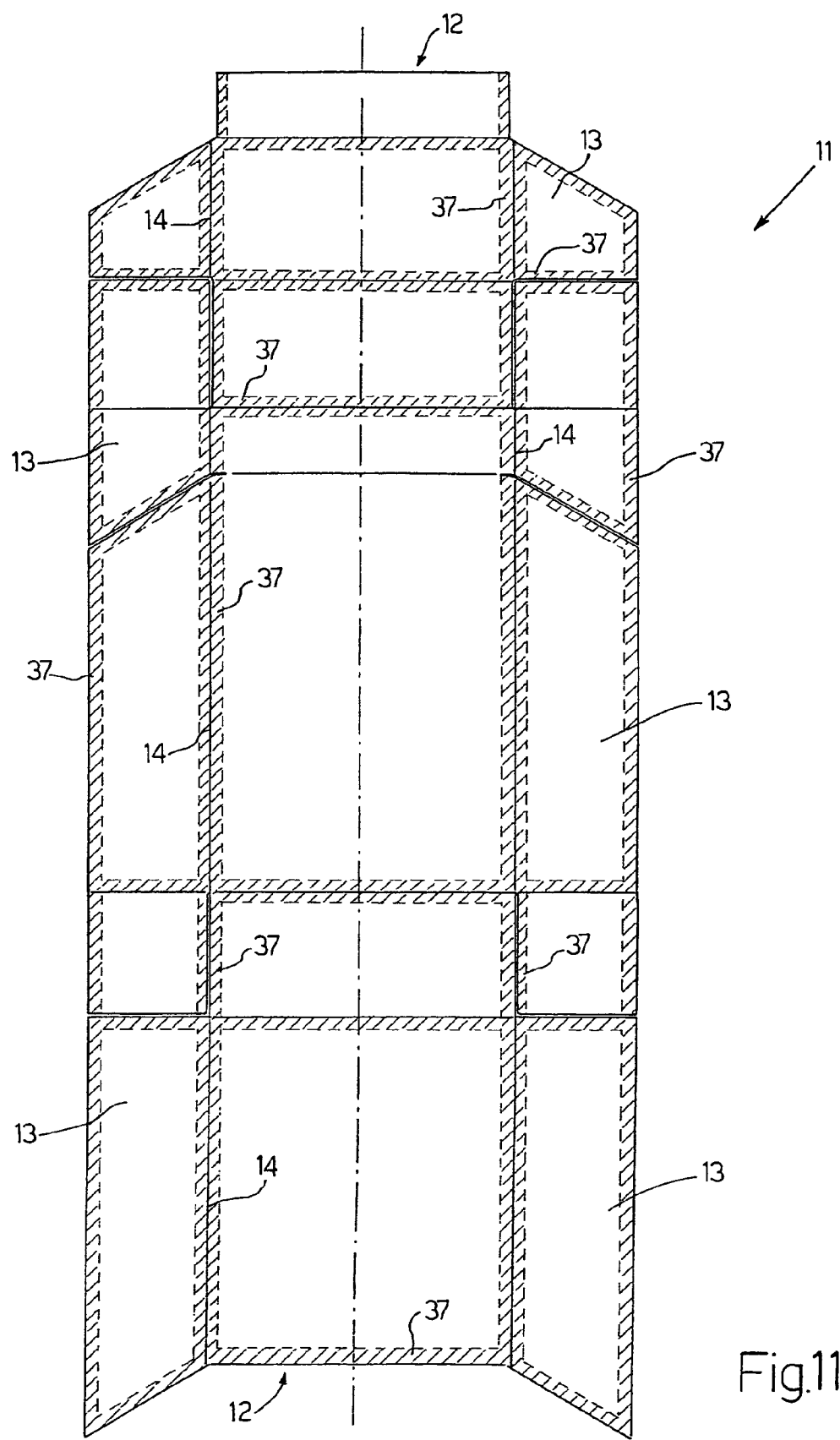

In the FIG. 6 packet 2, formed from the FIG. 11 blank 11, portion 37 extends along the edges of packet 2. As shown in FIG. 11, portion 37 extends at least partly along the edge of blank 11. In FIGS. 6 and 11, portion 37 is hatched.

Figure 13:
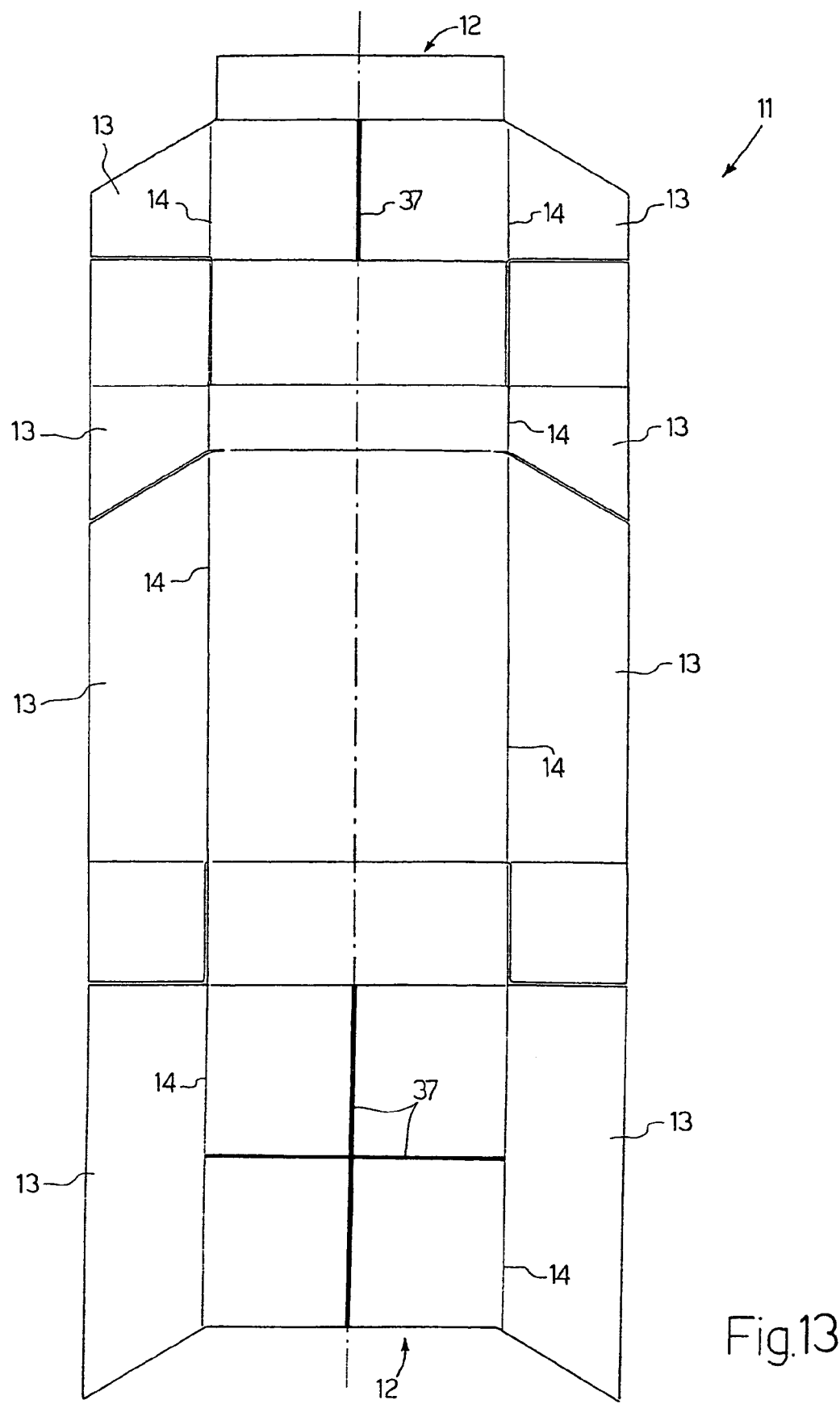

In the FIG. 8 packet 2, formed from the FIG. 13 blank 11, portion 37 comprises two substantially perpendicular lines on front wall 5, one extending from one longitudinal edge 8 to the other longitudinal edge 8, and the other extending from edge 9 to edge 10. In FIGS. 8 and 13, portion 37 is shown by bold lines.

Figure 12:
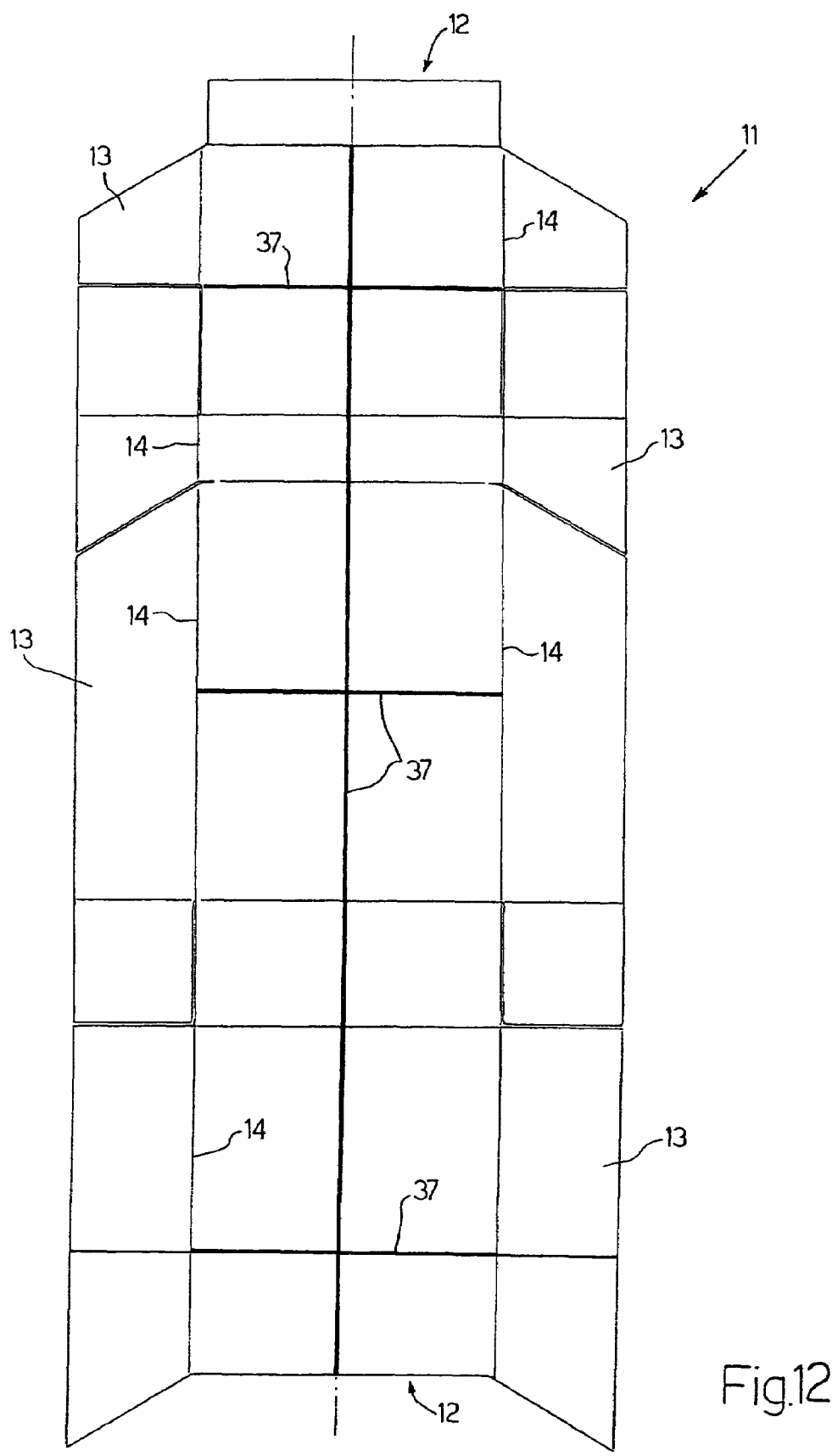

In the FIG. 7 packet 2, formed from the FIG. 12 blank 11, portion 37 comprises two substantially perpendicular lines, a first extending on front wall 5, lateral walls 6, and the rear wall (not shown in FIG. 7) of cup-shaped body 3, and a second extending on front walls 5 and 5a, on the bottom and rear walls (not shown in FIG. 7) of cup-shaped body 3, and on top wall 7 and the rear wall (not shown in FIG. 7) of lid 4. In FIGS. 7 and 12, portion 37 is shown by bold lines.

Figure 9:
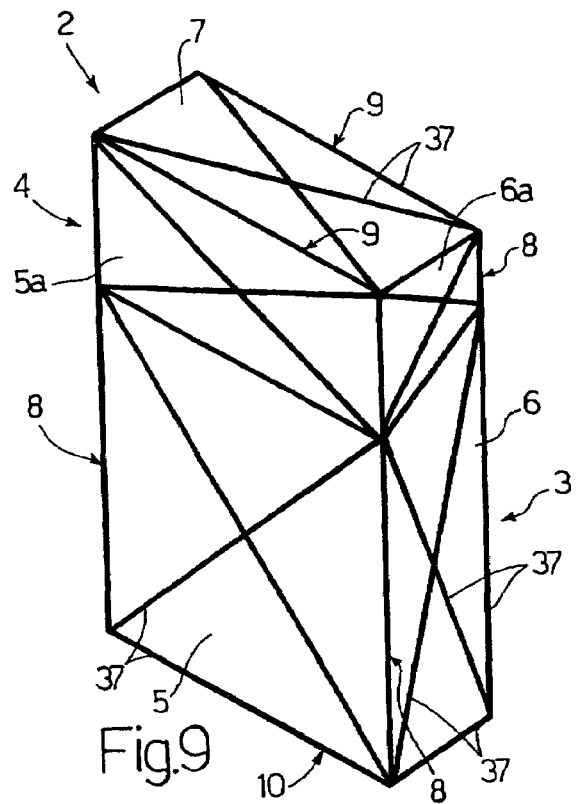
Figure 14:
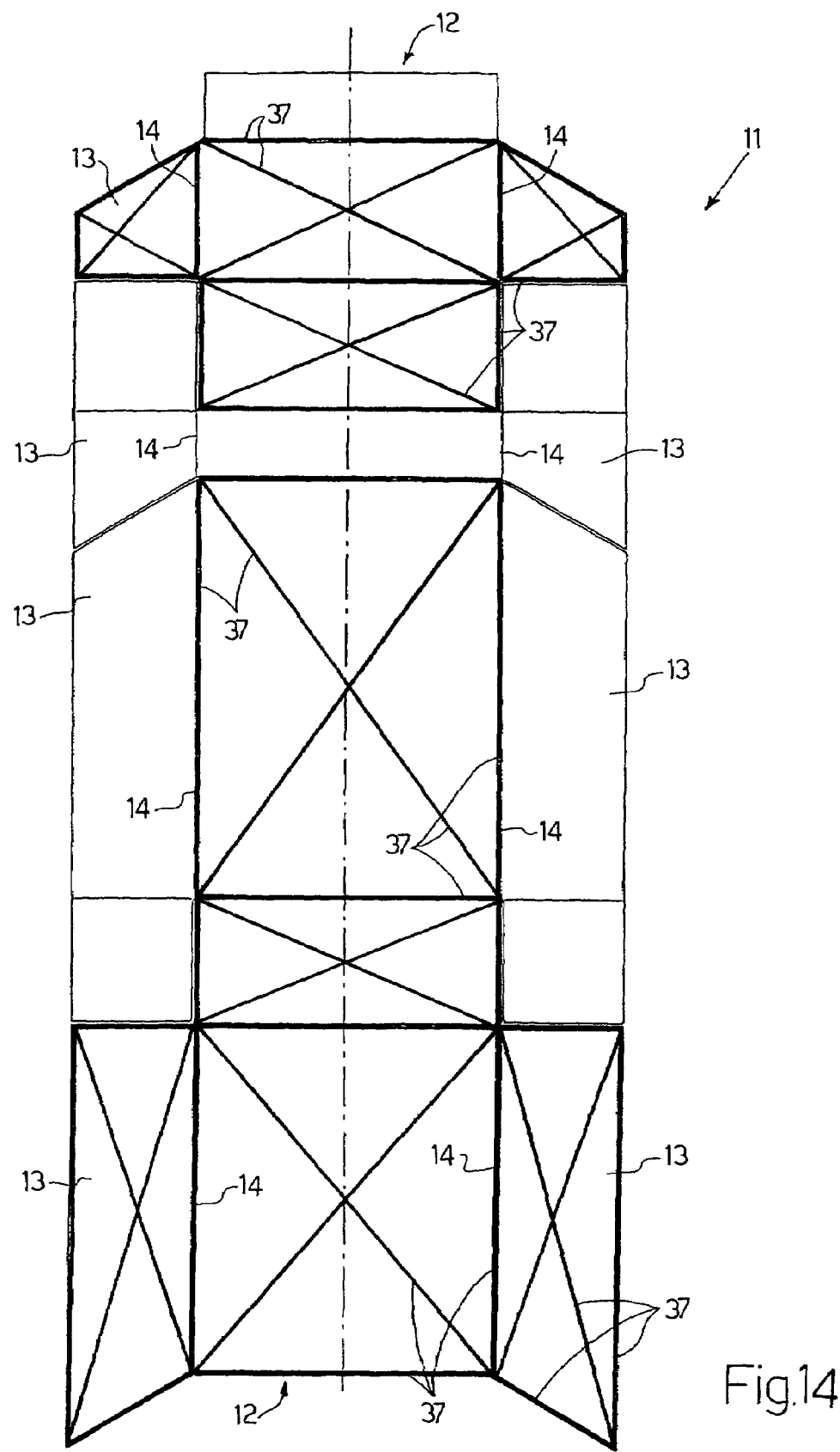

The FIG. 9 packet 2, formed from the FIG. 14 blank 11, has a portion 37 comprising a number of lines, which extend along the edges of packet 2, and which, from the corners, intersect on each wall 5, 5a, 6, 6a, 7, each of the rear walls (not shown), and the bottom wall (not shown). In FIGS. 9 and 14, portion 37 is shown by bold lines.

Though the above description and accompanying drawings relate to a conventional hinged-lid packet of cigarettes, the teachings of the present invention obviously also apply to packets of cigarettes of any type, such as a hinged-lid packet with rounded or bevelled edges, or a "soft" packet of cigarettes. The teachings of the present invention obviously also apply to cartons of packets of cigarettes, and to packets of other than cigarettes, such as packets of food products, confectionary, or toiletries.

The invention claimed is:

1. A method of quality controlling a packet; the method comprising:
   a feed step to feed the packet along a feed path through a quality control station;
   an optical detecting step to detect at least one detected data item relative to at least one given portion of the packet; and
   a comparing step to compare the detected data item with at least one reference data item to determine rejection or acceptance of the packet;
   the given portion comprising at least a pigment, which is optically detectable only at at least one given wavelength outside the visible range;
   the optical detecting step further comprising detecting the detected data item by receiving electromagnetic radiation having said given wavelength outside the visible range from said pigment.

2. A method as claimed in claim 1, wherein the position of said given portion is detected at said detecting step; the detected position being compared with a reference position at said comparing step.

3. A method as claimed in claim 1, wherein the intensity of the electromagnetic radiation, at said given wavelength, from the given portion is detected at said detecting step; the detected intensity being compared with a reference intensity at said comparing step.

4. A method as claimed in claim 1, wherein the shape of said given portion is detected at said detecting step; the detected shape being compared with a reference shape at said comparing step.

5. A method as claimed in claim 1, wherein the given portion comprises at least one first line and at least one second line crosswise to the first line; the first and second line extending at least from a first edge to a second edge of the packet.

6. A method as claimed in claim 1, wherein the given portion comprises at least one first line, and at least one second line crosswise to the first line; the first line extending from a first edge to a second edge of the packet, and the second line extending from a third edge to a fourth edge of the packet.

7. A method as claimed in claim 1, wherein the given portion comprises a grid having a first number of lines parallel to one another, and a second number of lines parallel to one another and crosswise to the first number of lines.

8. A method as claimed in claim 1, wherein the given portion extends at least partly along at least one edge of the packet.

9. A method as claimed in claim 1, wherein the packet is formed from a blank; the given portion extending at least partly along at least part of the edge of the blank.

10. A method as claimed in claim 1, wherein said given wavelength is a wavelength in the ultraviolet range.

11. A method as claimed in claim 1, and comprising an irradiating step to irradiate said given portion and an emitting step, at which the pigment emits electromagnetic radiation at said given wavelength.

12. A method as claimed in claim 11, wherein, during the irradiating step, said given portion is irradiated with electromagnetic radiation having a wavelength different from said given wavelength.

13. A packet having at least one given portion comprising a pigment optically detectable only at at least one given wavelength outside the visible range; the given portion comprising at least one first line, and at least one second line crosswise to the first line; the first and second line extending at least from a first edge to a second edge of the packet.

14. A packet having a given portion comprising a pigment optically detectable only at at least one given wavelength outside the visible range; the given portion comprising at least one first line and at least one second line crosswise to the first line; the first line extending from a first edge to a second edge of the packet, and the second line extending from a third edge to a fourth edge of the packet.

15. A packet as claimed in claim 13, wherein the given portion comprises a grid having a first number of lines parallel to one another, and a second number of lines parallel to one another and crosswise to the first number of lines.

16. A packet as claimed in claim 13, wherein the given portion extends at least partly along at least one edge of the packet.

17. A packet as claimed in claim 13, wherein the packet is formed from a blank; the given portion extending at least partly along at least part of the edge of the blank.

18. A packet as claimed in claim 13, wherein said given wavelength is a wavelength in the ultraviolet range.

19. A blank for producing a packet, and comprising a given portion having a pigment optically detectable only at at least one given wavelength outside the visible range; the given portion comprising at least one first line, and at least one second line crosswise to the first line; the first and second line each extending at least from a first edge to a second edge of the packet.

20. A blank for producing a packet, and comprising a given portion having a pigment optically detectable only at at least one given wavelength outside the visible range; the given portion comprising at least one first line, and at least one second line crosswise to the first line; the first line extending from a first edge to a second edge of the packet, and the second line extending from a third edge to a fourth edge of the packet.

21. A blank as claimed in claim 19, wherein the given portion comprises a grid having a first number of lines parallel to one another, and a second number of lines parallel to one another and crosswise to the first number of lines.

22. A blank as claimed in claim 19, wherein the given portion extends at least partly along at least one fold line of the blank.

23. A blank as claimed in claim 19, wherein the given portion extends at least partly along at least part of the edge of the blank.

24. A method of quality controlling a packet; the method comprising:
   a feed step to feed the packet along a feed path through a quality control station;
   an optical detecting step to detect at least one detected data item relative to at least one given portion of the packet; and
   a comparing step to compare the detected data item with at least one reference data item to determine rejection or acceptance of the packet;
   the given portion comprising at least a pigment, which is optically detectable only at at least one given wavelength lower than 400 nm and higher than 750 nm;

the optical detecting step further comprising detecting the detected data item by receiving electromagnetic radiation having said given wavelength from said pigment.

25. A method of quality controlling a packet; the method comprising:
- a feed step to feed the packet along a feed path through a quality control station;
- an optical detecting step to detect at least one detected data item relative to at least one given portion of the packet; and
- a comparing step to compare the detected data item with at least one reference data item to determine rejection or acceptance of the packet;
- said given portion comprising a grid having a plurality of first lines parallel to one another, and a plurality of second lines parallel to one another and crosswise to the first lines;
- the first lines extending from a first edge to a second edge of the packet, and the second lines extending from a third edge to a fourth edge of the packet;
- the given portion comprising at least a pigment, which is optically detectable only at at least one given wavelength outside the visible range;
- the optical detecting step further comprising detecting the detected data item by receiving electromagnetic radiation having said given wavelength outside the visible range from said pigment.

26. A method of quality controlling a packet; the method comprising:
- a feed step to feed the packet along a feed path through a quality control station;
- an optical detecting step to detect at least one detected data item relative to at least one given portion of the packet; and
- a comparing step to compare the detected data item with at least one reference data item to determine rejection or acceptance of the packet;
- said given portion the given portion extends at least partly along at least one edge of the packet;
- the given portion comprising at least a pigment, which is optically detectable only at at least one given wavelength outside the visible range;
- the optical detecting step further comprising detecting the detected data item by receiving electromagnetic radiation having said given wavelength outside the visible range from said pigment.

27. A method of quality controlling a packet; the method comprising:
- a feed step to feed the packet along a feed path through a quality control station;
- an optical detecting step to detect at least one detected data item relative to at least one given portion of the packet; and
- a comparing step to compare the detected data item with at least one reference data item to determine rejection or acceptance of the packet;
- the packet being formed from a blank;
- the given portion extending at least partly along at least part of the edge of the blank;
- the given portion comprising at least a pigment, which is optically detectable only at at least one given wavelength outside the visible range;
- the optical detecting step further comprising detecting the detected data item by receiving electromagnetic radiation having said given wavelength outside the visible range from said pigment.

* * * * *